United States Patent
Klein et al.

(10) Patent No.: US 10,330,588 B2
(45) Date of Patent: Jun. 25, 2019

(54) REAL TIME NUMERICAL COMPUTATION OF CORROSION RATES FROM CORROSION SENSORS

(71) Applicant: INTERNATIONAL BUSINESS MACHINES CORPORATION, Armonk, NY (US)

(72) Inventors: Levente I. Klein, Tuckahoe, NY (US); Dennis G. Manzer, Bedford Hills, NY (US)

(73) Assignee: International Business Machines Corporation, Armonk, NY (US)

(*) Notice: Subject to any disclaimer, the term of this patent is extended or adjusted under 35 U.S.C. 154(b) by 1023 days.

(21) Appl. No.: 13/710,839

(22) Filed: Dec. 11, 2012

(65) Prior Publication Data

US 2014/0163903 A1 Jun. 12, 2014

(51) Int. Cl.
*G01N 17/04* (2006.01)
*G01N 17/02* (2006.01)
*G06F 17/18* (2006.01)

(52) U.S. Cl.
CPC .......... *G01N 17/043* (2013.01); *G01N 17/02* (2013.01); *G01N 17/04* (2013.01); *G06F 17/18* (2013.01)

(58) Field of Classification Search
CPC ...... G01N 17/043; G01N 17/02; G01N 17/04; G06F 17/18
See application file for complete search history.

(56) References Cited

U.S. PATENT DOCUMENTS

| | | | | |
|---|---|---|---|---|
| 6,495,833 B1* | 12/2002 | Alfano | ............... | G01N 21/4795 250/330 |
| 6,906,257 B2* | 6/2005 | Saccomanno | ....... | C03C 17/3607 174/36 |
| 7,282,928 B1* | 10/2007 | Hladky | .................. | G01N 17/02 204/404 |
| 2005/0122121 A1* | 6/2005 | Gilboe | ................... | G01N 17/04 324/700 |
| 2005/0148081 A1* | 7/2005 | Braunling | ............ | G01N 17/043 436/6 |
| 2006/0162431 A1* | 7/2006 | Harris | .................. | G01N 17/006 73/86 |
| 2008/0048103 A1* | 2/2008 | Lee | ..................... | G01N 21/7703 250/227.18 |
| 2009/0184003 A1* | 7/2009 | Hammonds | ............ | G01N 17/04 205/775.5 |
| 2014/0114609 A1* | 4/2014 | Maurer | .............. | H03H 21/0016 702/179 |

OTHER PUBLICATIONS

"Particulate and Gaseous Contamination Guidelines for Data Centers" American Society of Heating, Refrigerating and Air-Conditioning Engineers, 2009.*

(Continued)

*Primary Examiner* — John C Kuan
(74) *Attorney, Agent, or Firm* — Tutunjian & Bitetto, P.C.; Vazken Alexanian (57) ABSTRACT

A method for determining a corrosion rate includes receiving an input signal including corrosion data from a sensor. A signal-to-noise ratio (SNR) and a type of noise is determined from the input signal. A corrosion rate computation method is selected based on the SNR and the type of noise. The corrosion rate is determined, using a processor, based on a selected corrosion rate computation method.

17 Claims, 3 Drawing Sheets

(56) References Cited

OTHER PUBLICATIONS

Chen, M., et al. "On Realizations of Least-Squares Estimation and Kalman Filtering by Systolic Arrays" NASA Astrophysics Data System, Survey of the State-of-the-Art and Focused Research in Range Systems, Task 2. Jun. 1986. (10 Pages)
Chiang, T., et al. "Hierarchical HDTV/SDTV Compatible Coding Using Kalman Statistical Filtering" IEEE Transactions on Circuits and Systems for Video Technology, vol. 9, No. 3. Apr. 1999. pp. 424-437.
Vahidi, A., et al. "Recursive Least Squares With Forgetting for Online Estimation of Vehicle Mass and Road Grade: Theory and Experiments" Vehicle System Dynamics, vol. 43, No. 1. Jan. 2005. pp. 1-28.
Wang, S., et al. "A Noise Reduction Method for Discrete Chaotic Signals and Its Application in Communication" IEEE 4th International Congress on Image and Signal Processing. Oct. 2011. pp. 2303-2307.

\* cited by examiner

REAL TIME NUMERICAL COMPUTATION OF CORROSION RATES FROM CORROSION SENSORS

GOVERNMENT RIGHTS

This invention was made with Government support under Contract No.: DE-EE0002897 awarded by the U.S. Department of Energy. The Government has certain rights to this invention.

BACKGROUND

Technical Field

The present invention relates to corrosion rate computation from corrosion sensors, and more particularly to the real time numerical computation of corrosion rates from a large number of corrosion sensors.

Description of the Related Art

Reactive monitoring of corrosion is based upon measuring a metal film transformation of copper and silver traces as they react with contamination gases. There are many ways to measure the corrosion rate. One way to measure the corrosion rate is to measure the change of electrical resistance for a metal film. A second way to measure the corrosion rate is to measure a frequency shift of a mass balance that has the metal deposited on it. Another way to measure the corrosion rate relies on measuring the mass of a metal coupon before and after exposure to the contaminated atmosphere. The metal film in the above approaches is consumed as the metal is transformed to a corrosion product. In many commercial implementations, there is thus a tradeoff between the lifetime of the sensor and the sensitivity of detection.

Measuring the corrosion rate is based upon determining the slope for the change in metal film thickness over time. If the change in film thickness is significant, the slope can be calculated relatively easily. However, if the change in film thickness is small, a longer time interval should be considered to have a detectable change in film thickness.

The rate of corrosion may vary by an order of magnitude from one location to another in a data center due to spatial and temporal variations, such as air flow, pollutant concentrations, temperature variations, etc. To accurately calculate corrosion rates that may vary from 20 Angstroms (A)/month up to 1000 A/month, the corrosion sensor should be made sensitive enough to pick up small changes in corrosion (the lowest limit is 1 A, which would be a single atom in thickness) and the computation of the corrosion rate should be adaptable to all of the conditions. For conventional corrosion rate computations, such as those based on resistive sensors, temperature and relative humidity variations may lead to inaccurate readings and should be compensated for. At lower corrosion rates (e.g., less than 20 A/month), quantization noise from measurements and temperature measurement noise may also result in inaccurate corrosion rate calculations if the rate is calculated frequently (e.g., every 15 minutes).

SUMMARY

A method for determining a corrosion rate includes receiving an input signal including corrosion data from a sensor. A signal-to-noise ratio (SNR) and a type of noise is determined from the input signal. A corrosion rate computation method is selected based on the SNR and the type of noise. The corrosion rate is determined, using a processor, based on a selected corrosion rate computation method.

A computer readable storage medium comprises a computer readable program for determining a corrosion rate. The computer readable program when executed on a computer causes the computer to perform the following steps. An input signal is received including corrosion data from a sensor. A signal-to-noise ratio (SNR) and a type of noise is determined from the input signal. A corrosion rate computation method is selected based on the SNR and the type of noise. The corrosion rate is determined, using a processor, based on a selected corrosion rate computation method.

A system for determining a corrosion rate includes a signal-to-noise ratio (SNR) determination module configured to determining a SNR and a type of noise from an input signal, the input signal including corrosion data from a sensor. A corrosion determination module is configured to select a module for corrosion rate computation based on the SNR and the type of noise. The corrosion determination module is further configured to determine, using a processor, the corrosion rate based on a selected corrosion rate computation module.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

In accordance with the present principles, systems and methods for real time numerical computation of corrosion rates from corrosion sensors are provided. An output of a corrosion sensor is received as an input. Preferably, the corrosion sensor measures the change of electrical resistance or change in the film thickness of a, e.g., silver or copper stamp. The corrosion sensor outputs the change in electrical resistance and the temperature.

The signal strength and noise of the input signal is determined to provide the signal-to-noise ratio (SNR) and the type of noise. Based on the SNR and the type of noise, at least one of Kalman filtering and least square fitting (LSF) with QR decomposition is performed on the input signal. In one embodiment, Kalman filtering is applied where the type of noise is Gaussian while LSF is applied for non-Gaussian noise (e.g., quantization noise). In another embodiment, Kalman filtering is applied for a large SNR (e.g., 1 or more) while LSF is applied for a small SNR (e.g., less than 1). Other embodiments are also contemplated.

Preferably, LSF is performed using a forgetting factor to decay away older data. Advantageously, older data is scaled such that less data is used to compute an updated corrosion rate. The forgetting factor may be adapted based upon the input signal. In one embodiment, for a low corrosion rate with noisy data, a forgetting factor close to 1 may be applied such that the older data takes longer to decay away. In another embodiment, for a high corrosion rate, a smaller forgetting factor may be applied such that the older data decays away faster. The results of the Kalman filtering and LSF-QR may be combined by weighting each result (e.g., equally). The rate of corrosion is provided as an output.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wireline, optical fiber cable, RF, etc. or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B)

only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1:
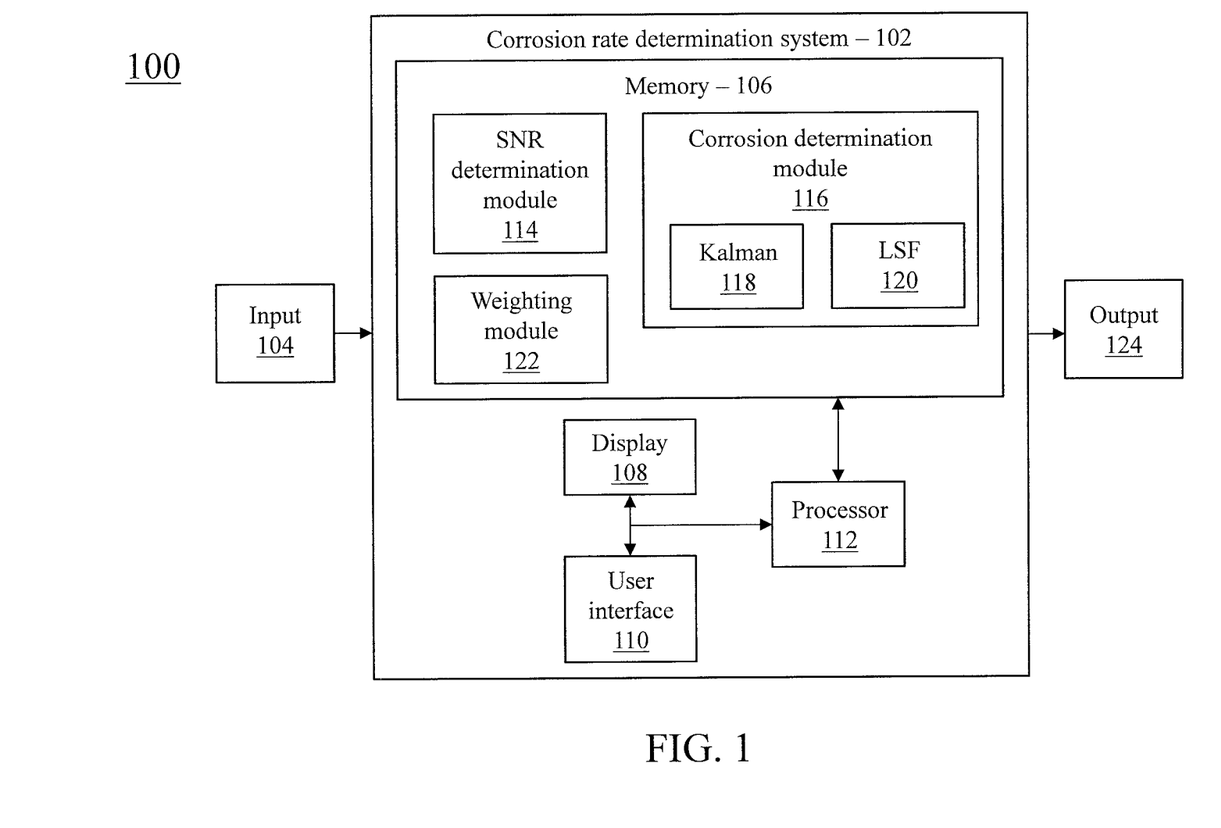
FIG. 1 is a block/flow diagram showing a system for determining a corrosion rate, in accordance with one illustrative embodiment.

Referring now to the drawings in which like numerals represent the same or similar elements and initially to FIG. 1, a block/flow diagram showing a system 100 for determining a corrosion rate is illustratively depicted in accordance with one embodiment. In one implementation, the present principles may be applied to determine a rate of corrosion to control the outdoor/indoor air mix for air conditioning units in data centers that use outside air for cooling. Other implementations are also contemplated.

The corrosion rate measurement system may include a workstation or system 102. The corrosion rate measurement system 102 preferably includes one or more processors 112 and memory 106 for storing programs, applications and other data. System 102 may include one or more displays 108 for viewing. The displays 108 may also permit a user to interact with the system 102 and its components and functions. This may be further facilitated by a user interface 110, which may include a keyboard, mouse, joystick, or any other peripheral or control to permit user interaction with the system 102. It should be understood that the functions and components of the system 102 may be integrated into one or more workstations or systems.

The system 102 may receive input 104, which may include an input signal. The input signal is preferably an output of a corrosion sensor; however, other sensor types are also contemplated. For example, in a preferred embodiment, the corrosion sensor measures the change of electrical resistance of a, e.g., silver or copper square of thin metal. The measure may be performed using, e.g., wireless remote technology. The corrosion sensor may output the change in electrical resistance and the temperature as an input 104 of the system 102. Data from a number of corrosion sensors (e.g., more than 100) may be analyzed in real-time to compute the corrosion rate. The corrosion thickness may be measured at varying intervals (e.g., from 1 second up to every hour). Preferably, the change in electrical resistance is compensated for temperature variations that occur around the sensors. For example, a known relationship between resistance and temperature may be applied to compensate for temperature variations using the temperature coefficient for, e.g., silver or copper traces. In another embodiment, the corrosion sensor determines the weight difference due to corrosion of a metal stamp placed in an environment for a week. Other embodiments of the corrosion sensors are also contemplated.

Memory 106 includes SNR (signal-to-noise ratio) determination module 114 configured to determine the signal strength and noise of the input signal 104. Based on the signal strength and noise, the SNR may be determined. Preferably, the signal would be the minimum measurement that would not be limited by noise. In addition, SNR determination module 114 determines a type of noise (e.g., Gaussian noise).

Memory 106 also includes corrosion determination module 116 configured to determine a rate of corrosion based upon the input signal 104. Corrosion determination module 116 may determine the corrosion rate using a Kalman filter 118 or a parameter estimation technique such as LSF (least square fit) 120. Preferably, based on the SNR and the type of noise determined by SNR determination module 114, at least one of Kalman filtering 118 and LSF 120 may be applied. For example, in one embodiment, Kalman filtering 118 may be applied for a large SNR (e.g., 1 or more) while LSF 120 may be applied for a small SNR (e.g., less than 1). In another example, Kalman filtering 118 may be applied where the noise is Gaussian noise while LSF 120 may be applied for non-Gaussian noise. Other embodiments are also contemplated.

It should be understood that corrosion determination module 116 is not limited to Kalman filter 118 and LSF 120, but may also include other corrosion rate determination techniques. For example, in one embodiment, corrosion determination module 116 may determine a rate of corrosion by gathering data from the input signal 104 for a fixed interval of time (e.g., 24 hours) and fitting a curve (or straight line) to the data. The slope of this line is a good approximation of the rate of corrosion. However, at each minute a new data point is received, an older data point is discarded and the fitting process must be carried out for the entire 24 hours of data. In addition, large amounts of data storage may be necessary to hold the matrices to perform the computations. Other corrosion determination techniques are also contemplated.

The system 102 may measure time in Unix time. Unix time measurements are time stamped in milliseconds from the year 1970. This may be a problem for double precision arithmetic since an additional minute from 1970 is insignificant. Therefore, all measurements should be displaced in time to one closer to the current date. Once the start time is determined, all data updates are measured relative to that starting time. Preferably, the start time is reset periodically, such as, e.g., once a year. Since the slope and intercept are available by calculation, it is possible to adjust these numbers to account for a new start time. However, it may be easier to restart the method from scratch with the new start time.

Kalman filtering 118 may be configured to determine optimal solutions in the face of noise. Kalman filtering 118 is configured to use a series of historical sensor data over time, which includes noise, to provide estimates of the corrosion rate. Kalman filtering 118 averages a prediction of the corrosion rate with new data using a weighted average. The purpose of the weights is that the values with better (i.e., smaller) estimated uncertainties are trusted more. The weights are calculated from the covariance, a measure of the estimated uncertainty of the prediction. The result of the weighted average is a new estimate of corrosion rate that lies in between the predicted and measured rate. This process is repeated at every time step, with the new estimate and its covariance informing the prediction used in the following iteration. As such, the Kalman filter 118 works recursively and only uses the last prediction, rather than the entire history, to predict an updated corrosion rate. However, Kalman filtering 118 assumes a Gaussian distribution of the noise. As such, Kalman filtering 118 is known to be poor for non-Gaussian noise (e.g., quantized noise).

LSF 120 may be configured to implement recursive least square (RLS) fit via updating QR decomposition. Least square fit-QR uses a small amount of data and is very fast. Suppose corrosion data values d1, d2 and d3 are taken at sequential time values t1, t2 and t3. The goal is to find the best least squares fit of a straight line to these data points. The Vandermonde matrix is formed as follows:

$$A = \begin{bmatrix} t1 & 1 \\ t2 & 1 \\ t3 & 1 \end{bmatrix}$$

and the data matrix is formed as follows:

$$D = \begin{bmatrix} d1 \\ d2 \\ d3 \end{bmatrix}.$$

To find the coefficients m and b corresponding to the straight line y=mx+b, QR decomposition is performed such that the matrix A is decomposed into a product A=QR of an orthogonal matrix Q and an upper triangular matrix R. The orthogonal matrix Q is found (by a sequence of Given Rotations) such that Q'A is upper triangle. Thus, by back substitution, it is possible to solve for the upper triangular part of Q'A for:

$$\begin{bmatrix} x & x \\ 0 & x \\ 0 & 0 \end{bmatrix} \begin{bmatrix} m \\ b \end{bmatrix} = Q'D = \begin{bmatrix} x \\ x \\ x \end{bmatrix}. \quad (1)$$

The value of m is the rate or slope of interest. Updating occurs when the next data point or points are received and the procedure is repeated as follows: only the first two rows of the upper triangular matrix and the first two rows of the right hand side of equation (1) are kept. The new data is appended as follows:

$$A = \begin{bmatrix} x & x \\ 0 & x \\ t4 & 0 \end{bmatrix}$$

$$D = \begin{bmatrix} x \\ x \\ d4 \end{bmatrix}.$$

The process is repeated (with two Givens Rotations to null out the bottom rows of A) and an updated solution is determined. This is repeated as new data is received.

If the process is repeated, the best fit for all data will be determined, and each data point will have equal weight. Since the goal of RLS is to estimate a moving target, a forgetting factor $\lambda$ is implemented for decaying away older data. One way to do this is to scale the left and right side of equation (1) by the forgetting factor $\lambda$ as follows:

$$\lambda \begin{bmatrix} x & x \\ 0 & x \\ 0 & 0 \end{bmatrix} \begin{bmatrix} m \\ b \end{bmatrix} = Q'D\lambda = \begin{bmatrix} x \\ x \\ x \end{bmatrix} \lambda.$$

The forgetting factor $\lambda$ scales down older data by $\lambda$ when $\lambda<1$, decreasing exponentially at every new iteration. Doing this repeatedly for each iteration causes the oldest data to be lost exponentially fast by powers of $\lambda$.

The forgetting factor $\lambda$ may be adapted based upon the signal strength and measurement noise. When the signal is noisy and the corrosion rate is very low, the forgetting factor should be close to 1 (i.e., it takes a long time to see any change and get an estimated rate, such that older data is forgotten slower). However, if the corrosion rate is high, the forgetting factor may be much smaller and the estimated corrosion rate will reflect a more up to date value (i.e., the older data is forgotten quicker). Adapting the forgetting factor can, thus, give estimates of the corrosion rates which vary hourly, when the rate is high and changing rapidly. When the corrosion rate is low, the forgetting factor may be increased towards 1 to extract the small signal from the noise. For example, a very low corrosion rate might warrant a factor of $\lambda=0.997$. However, a high corrosion rate might warrant a factor of $\lambda=0.92$.

Memory 106 may also include weighting module 122 configured to weight the results of Kalman filtering 118 and LSF 120 to provide the corrosion rate. For example, the weighting module 122 may weight each result equally. Other weightings are also contemplated. The corrosion rate may be provided as part of the output 124. Advantageously, the corrosion rate measurement system 102 provides a new update of the corrosion estimate at every sample, with minimum data transfer and storage.

Figure 2:
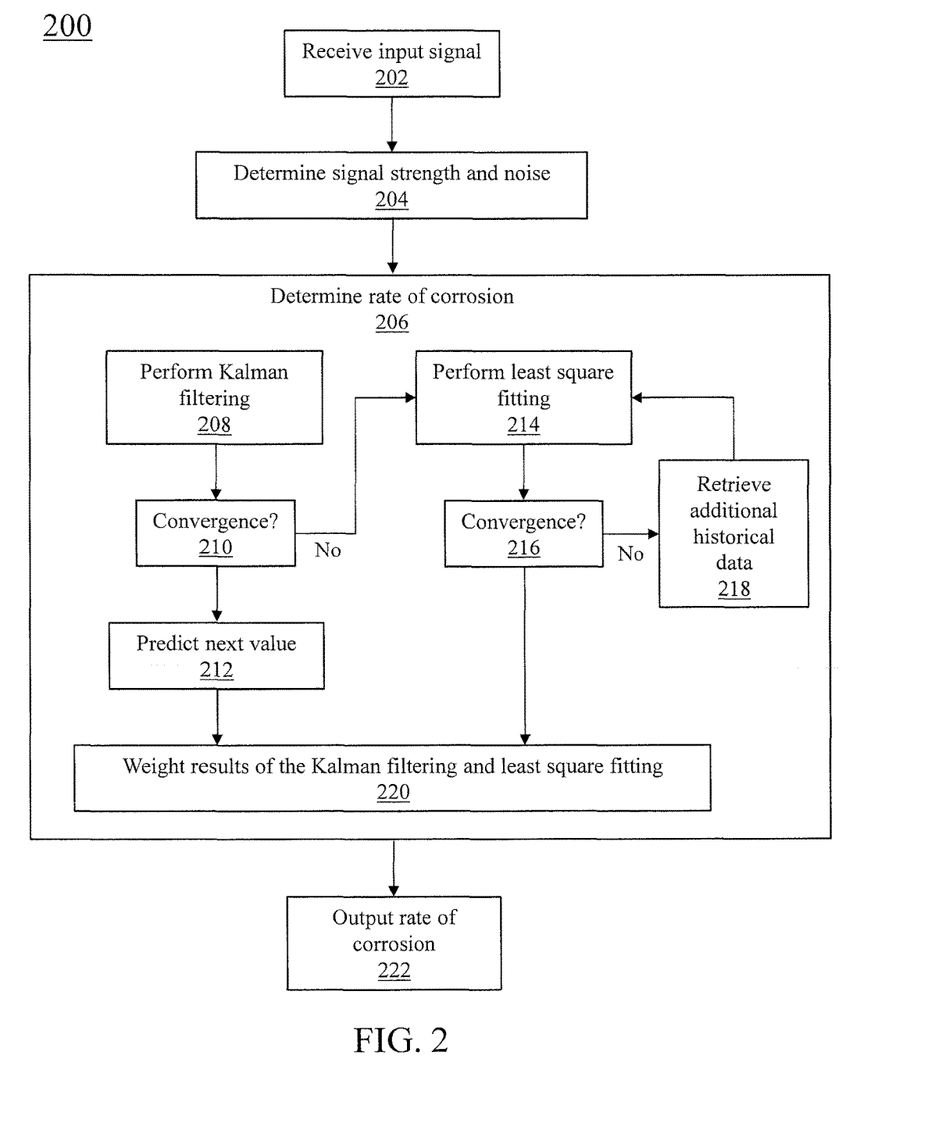
FIG. 2 is a block/flow diagram showing a method for determining a corrosion rate, in accordance with one illustrative embodiment.

Referring now to FIG. 2, a block/flow diagram showing a method 200 for determining a corrosion rate is illustratively depicted in accordance with one embodiment. In block 202, an output of a corrosion sensor is received as an input signal. It is noted that the present principles are not limited to the output of the corrosion sensor; rather, other sensor types and other input signals are also contemplated. In a preferred embodiment, the corrosion sensor measures the change in electrical resistance of a metal test sample (e.g., silver or copper). The corrosion sensor outputs the change in electrical resistance and the temperature as the input signal. The input signal may be received at intervals of every, e.g., second; however other intervals are also contemplated.

In block 204, the signal strength and noise of the input signal is determined to provide the SNR of the input signal and the type of noise (e.g., Gaussian). In block 206, a rate of corrosion is determined. Based upon the SNR and the type of noise, at least one of Kalman filtering is applied in block 208 and least square fitting is applied in block 214. In a preferred embodiment, LSF-QR is applied for a low SNR (e.g., less than 1) and/or non-Gaussian noise. Kalman filtering 208 may be applied for a high SNR (one or more) with Gaussian noise. Other embodiments are also contemplated.

Kalman filtering in block 208 provides estimates of the corrosion rate based upon historical data over time. Kalman filtering averages a prediction of the corrosion rate with new data from the input signal using a weighted average. If the Kalman filtering method converges in block 210, the updated predicted corrosion rate is provided in block 212. If the Kalman filtering method does not converge in block 210, least square fitting is applied in block 214.

Least square fitting is performed in block 214. Preferably, least square fitting is performed via QR decomposition. For a series of sensor data values determined at specified time points, the change of slope is determined to find the best fitting curve over the data points. As new sensor data is received, the older data is weighted by a forgetting factor. QR decomposition is performed and the slope and intercept are solved to determine a corrosion rate. In block 216, if the least square fitting by QR decomposition does not converge, additional historical data 218 is retrieved and least square fitting is performed in block 214.

In block 220, the results of the Kalman filtering and least square fitting are combined to provide a rate of corrosion in block 222. Preferably, the results of the Kalman filtering and the least square fitting are weighted.

Figure 3A:
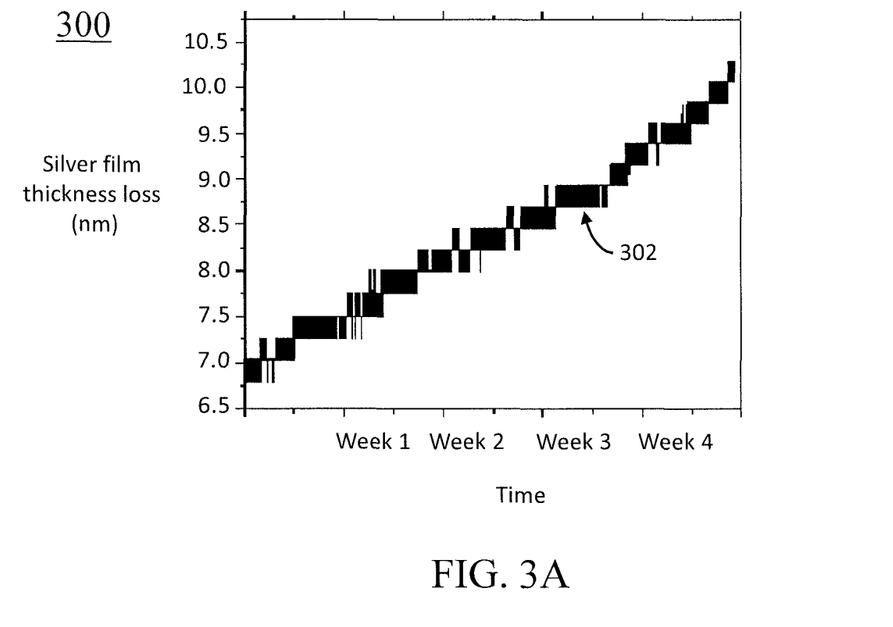
FIG. 3A shows a corrosion sensor output depicting silver film thickness loss over time, in accordance with one illustrative embodiment.

Referring now to FIG. 3A, a corrosion sensor output 300 depicting silver film thickness loss (in nanometers) over time (in weeks) is illustratively depicted in accordance with one illustrative embodiment. A corrosion rate may be determined at 65 A/month using the slope of the graph. However, the signal is digital noise limited at, e.g., period 302.

Figure 3B:
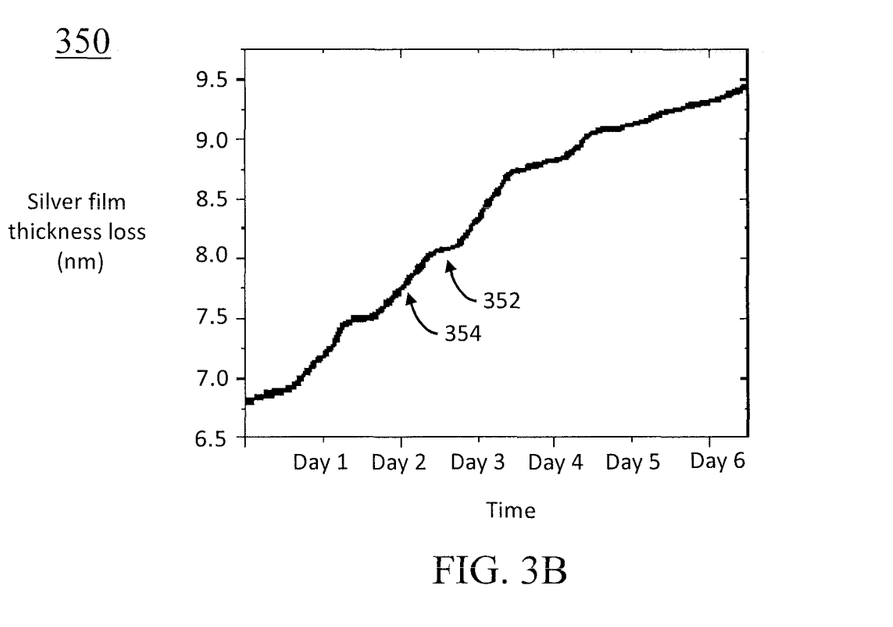
FIG. 3B shows a corrosion sensor output as applied to the present principles, in accordance with one illustrative embodiment.

Referring now to FIG. 3B, the corrosion sensor output 350 as applied to the present principles is depicted in accordance with one illustrative embodiment. A corrosion rate is determined by applying a least square fitting at, e.g., period 352 and a Kalman filtering at, e.g., period 354.

Having described preferred embodiments of a system and method for real time numerical computation of corrosion rates from corrosion sensors (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method for determining a corrosion rate, comprising:
    measuring, using a corrosion sensor, corrosion data, including electrical resistance and temperature, relating to a transformation of a metal article to a corroded state to generate an input signal;
    determining a signal-to-noise ratio (SNR) and a type of noise from the input signal;
    automatically selecting at least one corrosion rate computation method from a plurality of corrosion rate computation methods based on an association between the SNR and the type of noise and an accuracy of each of the plurality of computation methods given the SNR and the type of noise;
    determining a set of historical corrosion data according to the SNR, the type of noise and the selected at least one corrosion rate computation method;
    weighting each of the selected at least one corrosion rate computation method relative to each other of the selected at least one corrosion rate computation method;
    filtering the input signal with the selected at least one corrosion rate computation method according to the relative weighting to determine, using a processor, the corrosion rate based on a selected at least one corrosion rate computation method and the set of historical corrosion data; and
    evaluating corrosion of the metal article.

2. The method as recited in claim 1, wherein selecting the at least one corrosion rate computation method includes applying Kalman filtering where the type of noise is Gaussian noise.

3. The method as recited in claim 1, wherein selecting the at least one corrosion rate computation method includes applying least square fitting where the SNR is less than one and applying Kalman filtering where the SNR is one or more.

4. The method as recited in claim 1, wherein selecting the at least one corrosion rate computation method includes applying least square fitting by QR decomposition.

5. The method as recited in claim 1, wherein selecting the at least one corrosion rate computation method includes applying least square fitting using a forgetting factor to scale down past data.

6. The method as recited in claim 5, further comprising adapting the forgetting factor based upon the SNR.

7. The method as recited in claim 1, further comprising combining results of two or more corrosion rate computation methods by weighting the results.

8. The method as recited in claim 1, further comprising applying least square fitting where Kalman filtering does not converge.

9. The method as recited in claim 1, wherein the metal article is a metal film and the corrosion data relating to the transformation is a change in electrical resistance in the metal film relating to a change in metal film thickness as the metal film is transformed to a corrosion product.

10. The method as recited in claim 1, further comprising controlling an air mix in one or more air conditioning units in a data center based on the corrosion rate.

11. A non-transitory computer readable storage medium comprising a computer readable program for determining a corrosion rate, wherein the computer readable program when executed on a computer causes the computer to perform the method of claim 1.

12. A system for determining a corrosion rate, comprising:
    a corrosion sensor to measure corrosion data relating to a transformation of a metal article to a corroded state, including a change in electrical resistance of the metal article, to generate an input signal;
    a signal-to-noise ratio (SNR) determination module configured to determine a SNR and a type of noise from the input signal;
    a corrosion determination module configured to automatically select at least one module for corrosion rate computation from a plurality of modules for corrosion rate computation based on an association between the SNR and the type of noise and an accuracy of each of the plurality of modules for corrosion rate computation given the SNR and the type of noise, and to determine a set of historical corrosion data according to the SNR, the type of noise and the selected at least one corrosion rate computation method;
    a weighting module configured to weight each of the selected at least one corrosion rate computation method relative to each other of the selected at least one corrosion rate computation method;
    the corrosion determination module further configured to filter the input signal with the selected at least one corrosion rate computation method according to the relative weighting to determine, using a processor, the corrosion rate based on a selected corrosion rate computation module; and
    an output module configured to evaluate corrosion of the metal article.

13. The system as recited in claim 12, wherein the corrosion determination module includes a Kalman filtering module configured to apply Kalman filtering where the type of noise is Gaussian noise.

14. The system as recited in claim 12, wherein the corrosion determination module is further configured to apply least square fitting where the SNR is less than one and applying Kalman filtering where the SNR is one or more.

15. The system as recited in claim 12, wherein the corrosion determination module is further configured to apply least square fitting using a forgetting factor to scale down past data.

16. The system as recited in claim 15, wherein the corrosion determination module is further configured to adapt the forgetting factor based upon the SNR.

17. A computer-implemented method for reducing corrosion of data center components by determining a corrosion rate of the data center components, comprising:
   measuring, using a corrosion sensor, corrosion data, including electrical resistance and temperature, relating to a transformation of a metal article to a corroded state to generate an input signal;
   determining a signal-to-noise ratio (SNR) and a type of noise from the input signal;
   automatically selecting a corrosion rate computation method from a plurality of corrosion rate computation methods based on an association between the SNR and the type of noise and an accuracy of each of the plurality of computation methods given the SNR and the type of noise;
   controlling an air mix of outdoor air and indoor air in one or more air conditioning units in the data center based on the corrosion rate determined by the selected corrosion rate computation method.

* * * * *